United States Patent
Puett et al.

(10) Patent No.: US 12,190,436 B2
(45) Date of Patent: Jan. 7, 2025

(54) SYSTEMS AND METHODS FOR GENERATING MULTI-VIEW SYNTHETIC DENTAL RADIOGRAPHS FOR INTRAORAL TOMOSYNTHESIS

(71) Applicant: The University of North Carolina at Chapel Hill, Chapel Hill, NC (US)

(72) Inventors: Connor Puett, Durham, NC (US); Otto Z. Zhou, Chapel Hill, NC (US); Jianping Lu, Chapel Hill, NC (US); Christina Inscoe, Holly Springs, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 225 days.

(21) Appl. No.: 17/529,346

(22) Filed: Nov. 18, 2021

(65) Prior Publication Data
US 2022/0148252 A1 May 12, 2022

Related U.S. Application Data

(63) Continuation of application No. PCT/US2020/047319, filed on Aug. 21, 2020.
(Continued)

(51) Int. Cl.
*G06T 15/08* (2011.01)
*A61B 6/02* (2006.01)
(Continued)

(52) U.S. Cl.
CPC .............. *G06T 15/08* (2013.01); *A61B 6/025* (2013.01); *A61B 6/51* (2024.01); *G06T 5/70* (2024.01);
(Continued)

(58) Field of Classification Search
CPC ......... G06T 15/08; G06T 5/70; G06T 11/006; G06T 15/20; G06T 2207/10116;
(Continued)

(56) References Cited

U.S. PATENT DOCUMENTS

| 9,269,168 B2 | 2/2016 | Inglese et al. |
| 2008/0025583 A1* | 1/2008 | Jabri ............... G16H 40/63 600/407 |

(Continued)

FOREIGN PATENT DOCUMENTS

| JP | 2013240584 A | 12/2013 |
| JP | 2019514663 A | 6/2019 |

(Continued)

OTHER PUBLICATIONS

Japanese Office Action for Application No. 2021569837 dated Mar. 7, 2023.
(Continued)

*Primary Examiner* — Jose R Soto Lopez
(74) *Attorney, Agent, or Firm* — KDW FIRM PLLC

(57) ABSTRACT

Systems and methods for generating multi-view synthetic dental radiographs for intraoral tomosynthesis. In some embodiments, the method includes generating or receiving two-dimensional (2D) projection images, manipulating pixel values contained in each of the plurality of 2D projection images, reconstructing a three-dimensional (3D) image space from information available in the plurality of 2D projection images, the 3D image space comprising voxel values, manipulating the voxel values in the 3D image space using one or more tunable weighting algorithms that can be adjusted to emphasize one or more features of interest of each image in the 3D image space, generating a plurality of synthetic dental radiographs from multiple views using information available in the 3D image space, and displaying
(Continued)

one or more of the synthetic dental radiographs. In some embodiments, the system includes a display in communication with an image processing system comprising one or more processors for performing the method.

22 Claims, 12 Drawing Sheets

Related U.S. Application Data

(60) Provisional application No. 62/889,932, filed on Aug. 21, 2019.

(51) Int. Cl.
<table>
<tr><td>A61B 6/51</td><td>(2024.01)</td></tr>
<tr><td>G06T 5/70</td><td>(2024.01)</td></tr>
<tr><td>G06T 11/00</td><td>(2006.01)</td></tr>
<tr><td>G06T 15/20</td><td>(2011.01)</td></tr>
</table>

(52) U.S. Cl.
CPC ............ *G06T 11/006* (2013.01); *G06T 15/20* (2013.01); *G06T 2207/10116* (2013.01); *G06T 2207/20081* (2013.01); *G06T 2207/30036* (2013.01); *G06T 2210/41* (2013.01); *G06T 2211/424* (2013.01)

(58) Field of Classification Search
CPC . G06T 2207/20081; G06T 2207/30036; G06T 2210/41; G06T 2211/424; G06T 11/008; A61B 6/025; A61B 6/51; A61B 6/5258; A61B 6/5217; A61B 6/5235
See application file for complete search history.

(56) References Cited

U.S. PATENT DOCUMENTS

<table>
<tr><td>2008/0037843 A1</td><td></td><td>2/2008</td><td>Fu</td><td></td></tr>
<tr><td>2008/0069294 A1*</td><td></td><td>3/2008</td><td>Wigstrom</td><td>G06T 5/20<br>378/4</td></tr>
<tr><td>2017/0039734 A1</td><td></td><td>2/2017</td><td>Langan</td><td></td></tr>
<tr><td>2017/0281110 A1*</td><td></td><td>10/2017</td><td>Mandelkern</td><td>A61B 6/5264</td></tr>
<tr><td>2019/0164288 A1*</td><td></td><td>5/2019</td><td>Wang</td><td>G06T 7/0014</td></tr>
<tr><td>2019/0175131 A1*</td><td></td><td>6/2019</td><td>Duewer</td><td>A61B 6/025</td></tr>
</table>

FOREIGN PATENT DOCUMENTS

<table>
<tr><td>WO</td><td>2011156526 A2</td><td>12/2011</td></tr>
<tr><td>WO</td><td>WO 2012/177867 A2</td><td>12/2012</td></tr>
<tr><td>WO</td><td>2015015219 A1</td><td>2/2015</td></tr>
<tr><td>WO</td><td>WO 2017/196413 A1</td><td>11/2017</td></tr>
<tr><td>WO</td><td>WO 2019/040932 A1</td><td>2/2019</td></tr>
<tr><td>WO</td><td>WO 2021/035109 A1</td><td>2/2021</td></tr>
</table>

OTHER PUBLICATIONS

International Search Report and Written Opinion for Application No. PCT/US2020/047319 dated Dec. 3, 2020.

Gilbert, P. "Iterative Methods for the Reconstruction of Three-Dimensional Objects from Their Projections," Journal of Theoretical Biology, vol. 36, issue 1, pp. 105-117, Jul. 1972.

Dempster, A. et al., "Maximum Likelihood from Incomplete Data Via the EM Algorithm", Journal of the Royal Statistical Society, 39, 1-38. 1977.

Andersen, A.H. et al., "Simultaneous Algebraic Reconstruction Technique (Sart): A Superior Implementation of the ART Algorithm", Ultrasonic Imaging, vol. 6, issue 1, pp. 81-94, Jan. 1984.

Feldkamp, L.A. et al., "Practical Cone Beam Algorithm", Journal of the Optical Society of America A, vol. 1, issue 6, pp. 612-619, Jun. 1984.

European Office Action for Application No. 20853909 dated Aug. 23, 2023.

Korean Office Action for Application No. 1020227005305 dated Aug. 29, 2023.

Japanese Office Action for Application No. 2021569837 dated Jun. 13, 2023.

* cited by examiner

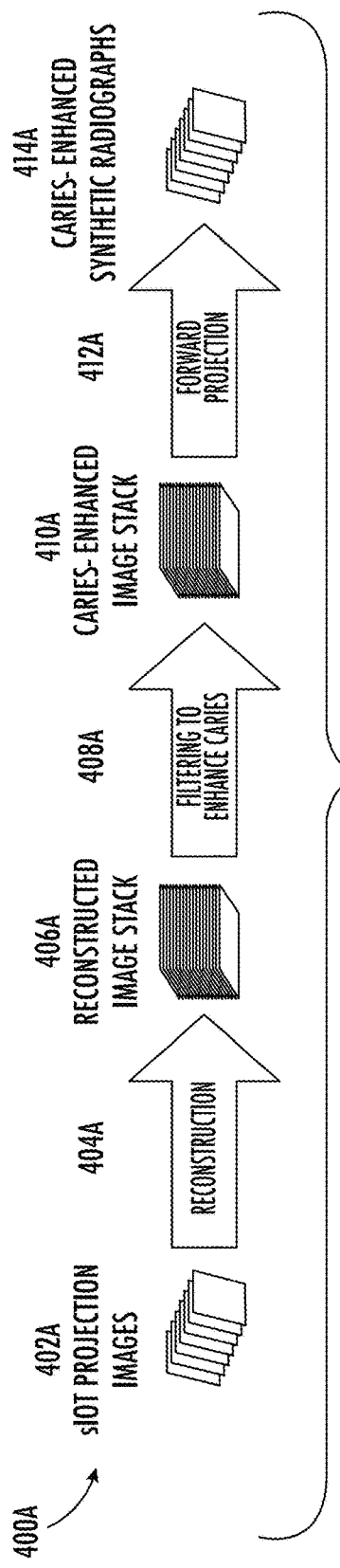
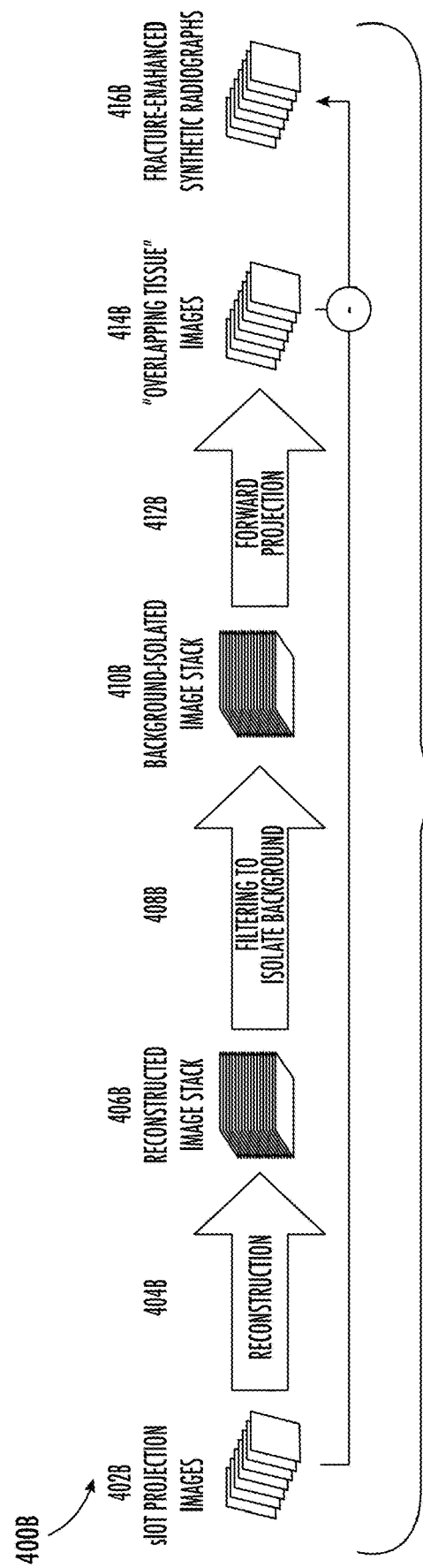
FIG. 4A
FIG. 4B

SYSTEMS AND METHODS FOR GENERATING MULTI-VIEW SYNTHETIC DENTAL RADIOGRAPHS FOR INTRAORAL TOMOSYNTHESIS

CROSS-REFERENCE TO RELATED APPLICATIONS

This patent application is a continuation of and claims priority to PCT/US2020/047319 filed Aug. 21, 2020, which claims priority to U.S. Provisional Patent Application Ser. No. 62/889,932, filed Aug. 21, 2019, the entire disclosures of which are incorporated by reference herein.

GOVERNMENT INTEREST

This invention was made with government support under Grant Number CA235892 awarded by the National Institutes of Health. The government has certain rights in the invention.

TECHNICAL FIELD

The subject matter disclosed herein relates generally to the display of information collected by intraoral tomosynthesis. More particularly, the subject matter disclosed herein relates to systems and methods to generate multi-view synthetic dental radiographs.

BACKGROUND

Typically referred to as cavities or caries, tooth decay is the most common dental disease, affecting the vast majority of Americans by adulthood. Since caries occur frequently in sites that cannot be directly visualized, x-ray imaging has become a standard screening tool. In fact, screening by dental radiography for caries is the only x-ray study approved by the Food and Drug Administration (FDA) for regular use from childhood through adulthood. Intraoral radiography, which refers to the location of the detector in the mouth, is the standard approach. It is performed routinely in the dental office to screen for caries and is also used for a host of other diagnostic purposes. However, the ability of intraoral radiography to detect many common dental conditions remains relatively low, since superimposed bone, tooth, and metal often hide pathology. In fact, the sensitivity for detecting caries ranges from only 40% to 70%, depending on the location of the lesion. Similarly, the detection of vertical root fractures associated with endodontic therapy, the assessment of periodontal disease, and the identification of bone resorption adjacent to dental implant posts have all been shown to be compromised by the problem of superposition.

Imaging technologies capable of providing a larger field-of-view and/or depth information have been developed. Panoramic radiographs and computed tomography (CT) are available. However, with both techniques, the detector is positioned outside the mouth and rotates around the patient's head while collecting x-rays generated by a moving x-ray source. The in-plane image resolution of these techniques is lower than that of intraoral radiography, and panoramic radiography introduces distortions into the image, limiting its applicability. CT exposes the head and neck to a relatively high radiation dose and requires expensive equipment as well as specialized training to operate the machines and interpret the images. Also, the frequent appearance of streak artifacts in CT images, especially in the presence of metallic hardware, can limit its diagnostic accuracy. As such, panoramic radiographs and CT are used for specific diagnostic purposes, not routine screening.

Tuned-aperture computed tomography (TACT) is a technique introduced to gather some depth information while maintaining the intraoral location of the detector. With this approach, a single moveable x-ray source is positioned at different angles relative to the mouth and a series of two-dimensional (2D) images are obtained. Markers located in the field-of-view allow for the calculation of the geometry after imaging, providing a method for reconstructing the images into a three-dimensional (3D) image space. Although TACT has been shown to improve the visibility of dental pathology, including caries, the approach is time-consuming and requires additional training to acquire and then interpret the images. As a result, TACT is not ideal for incorporation into a busy dental office. Indeed, there continues to be a need for a practical 3D imaging approach that fits into the workflow of the dental clinic. Intraoral tomosynthesis appears to be a viable and promising option.

Similar to TACT, intraoral tomosynthesis acquires a series of 2D images from different angles relative to the mouth. However, the geometry of an intraoral tomosynthesis system is pre-determined and fixed, and therefore the 3D image space can be reconstructed without markers in the field-of-view, thereby eliminating the time-consuming steps associated with TACT. The processing method described herein relates to the generation of a series of 2D synthetic dental radiographs from multiple angles using the information collected by intraoral tomosynthesis.

The general concept of displaying information collected by tomosynthesis in 3D and also synthetic 2D images was pioneered in breast imaging, in which a single synthetic 2D image is often generated to improve the detection of microcalcifications. However, the purpose for generating multi-view synthetic dental radiographs to display the information collected by intraoral tomosynthesis is quite different and reflects the frequent need to see around dense objects in the mouth, including bone, tooth enamel, and metal, in order the visualize a site-of-concern. The processing method disclosed herein is therefore unique, as it was developed to address this unique need in dental imaging by taking advantage of the information collected by intraoral tomosynthesis.

SUMMARY

In accordance with this disclosure, systems and methods for generating one or more multi-view synthetic dental radiographs are provided. In one aspect, a method for generating one or more multi-view synthetic dental radiographs using a chain of interdependent image processing steps is provided, the method comprising: generating or receiving a plurality of two-dimensional (2D) projection images; manipulating pixel values contained in each of the plurality of 2D projection images; reconstructing a three-dimensional (3D) image space from information available in the plurality of 2D projection images, the 3D image space comprising voxel values; manipulating the voxel values in the 3D image space using one or more tunable weighting algorithms that can be adjusted to emphasize one or more features of interest of each image in the 3D image space; generating a plurality of synthetic dental radiographs from multiple views using information available in the 3D image space; and displaying one or more of the plurality of synthetic dental radiographs.

In some embodiments, the method further comprises manipulating pixel values in the plurality of synthetic dental radiographs. In some embodiments, manipulating pixel values contained in each of the plurality of 2D project images comprises: segmenting artifact-producing features in each of the plurality of 2D projection images prior to reconstructing the 3D image space; assigning pixel values to segmented regions by inward interpolation from surrounding pixel values for each of the plurality of 2D projections, thereby reducing artifacts caused by the artifact-producing features. In some embodiments, the method further comprises fusing the artifact-producing features segmented from the 2D projection images back into the synthetic dental radiographs. In some embodiments, the 3D image space is generated using analytical or iterative reconstruction algorithms customized to intraoral tomosynthesis.

In some embodiments, the method further comprises identifying and/or enhancing features of interest, using filters and/or deep-learning techniques, features of interest including dental caries or dental fractures in the 3D image space. In some embodiments, the plurality of synthetic dental radiographs represent a range of viewing perspectives that may or may not depict a same angle from which the original x-ray projections were acquired. In some embodiments, different weighting algorithms are applied to the 3D image space to enhance features of interest, such as caries or fractures, with each weighting algorithm producing a unique set of multi-view synthetic dental radiographs. In some embodiments, enhancing fractures comprises emphasizing higher-frequency components of an image and enhancing caries comprising emphasizing lower-frequency components of the image. In some embodiments, the method further comprises optimizing the plurality of synthetic dental radiographs using filters customized to dental imaging. In some embodiments, reconstructing the 3D image space comprises using one or more of the following reconstruction techniques: filtered back projection (FBP), simultaneous iterative reconstruction technique (SIRT), simultaneous algebraic reconstruction technique (SART), or maximum likelihood expectation maximization (MLEM).

In another aspect, the subject matter of the present disclosure further comprises a method for generating one or more multi-view synthetic dental radiographs, the method comprising: positioning an intraoral x-ray detector in a subject's mouth; determining a position of the intraoral x-ray detector relative to one or more x-ray source; capturing one or more x-ray projections from multiple viewing angles relative to the intraoral x-ray detector; transferring the one or more x-ray projection images to one or more processors; manipulating, by the one or more processors, pixel values contained in the one or more x-ray projection images; reconstructing a 3D image space from information available in the one or more x-ray projection images, the 3D image space comprising voxel values; manipulating the voxel values in the 3D image space using one or more tunable weighting algorithms that can be adjusted to highlight specific image features in each image in the 3D image space; generating a plurality of synthetic dental radiographs from multiple views using information available in the 3D image space; and displaying one or more of the plurality of synthetic dental radiographs.

In another aspect, the subject matter of the present disclosure describes a system for generating one or more multi-view synthetic dental radiographs, the system comprising: a display in communication with an image processing system comprising one or more processors; wherein the image processing system is configured to: receive a plurality of two-dimensional (2D) projection images; manipulate pixel values contained in each of the plurality of 2D projection images; reconstruct a three-dimensional (3D) image space from information available in the plurality of 2D projection images, the 3D image space comprising voxel values; manipulate the voxel values in the 3D image space using one or more tunable weighting algorithms that can be adjusted to emphasize features of interest of each image in the 3D image space; generate a plurality of synthetic dental radiographs from multiple views using information available in the 3D image space; and display one or more of the plurality of synthetic dental radiographs on the display.

In some embodiments, the image processing system is further configured to: segment artifact-producing features in each of the plurality of 2D projection images prior to reconstructing the 3D image space; and assign pixel values to segmented regions of each of the plurality of 2D projection images by inward interpolation from surrounding pixel values. In some embodiments, the image processing system is further configured to fuse back the artifact-producing features segmented from the 2D projection images into the synthetic dental radiographs. In some embodiments, the 3D image space is generated using analytical or iterative reconstruction algorithms customized to intraoral tomosynthesis. In some embodiments, the image processing system is further configured to identify and/or enhance features of interest, using filters and/or deep-learning techniques, including dental caries or dental fractures in the 3D image space.

In some other embodiments, the plurality of synthetic dental radiographs represent a range of viewing perspectives that may or may not depict a same angle from which the original x-ray projections were acquired. In some embodiments, the image processing system is further configured to apply different weighting algorithms to the 3D image space to enhance features of interest, such as caries or fractures, with each weighting algorithm producing a unique set of multi-view synthetic dental radiographs. In some embodiments, wherein the image processing system is configured to enhance fractures by emphasizing higher-frequency components of an image; and wherein the image processing system is configured to enhance caries by emphasizing lower-frequency components of an image. In some embodiments, the image processing system is further configured to optimize the plurality of synthetic dental radiographs using filters customized to dental imaging. In some embodiments, the image processing system is configured to reconstruct the 3D image space using one or more of the following filter techniques: filtered back projection (FBP), simultaneous iterative reconstruction technique (SIRT), simultaneous algebraic reconstruction technique (SART), or maximum likelihood expectation maximization (MLEM).

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 4A and FIG. 4B are flow charts illustrating various steps in the process of some embodiments of the present disclosure;

DETAILED DESCRIPTION

Figure 1:
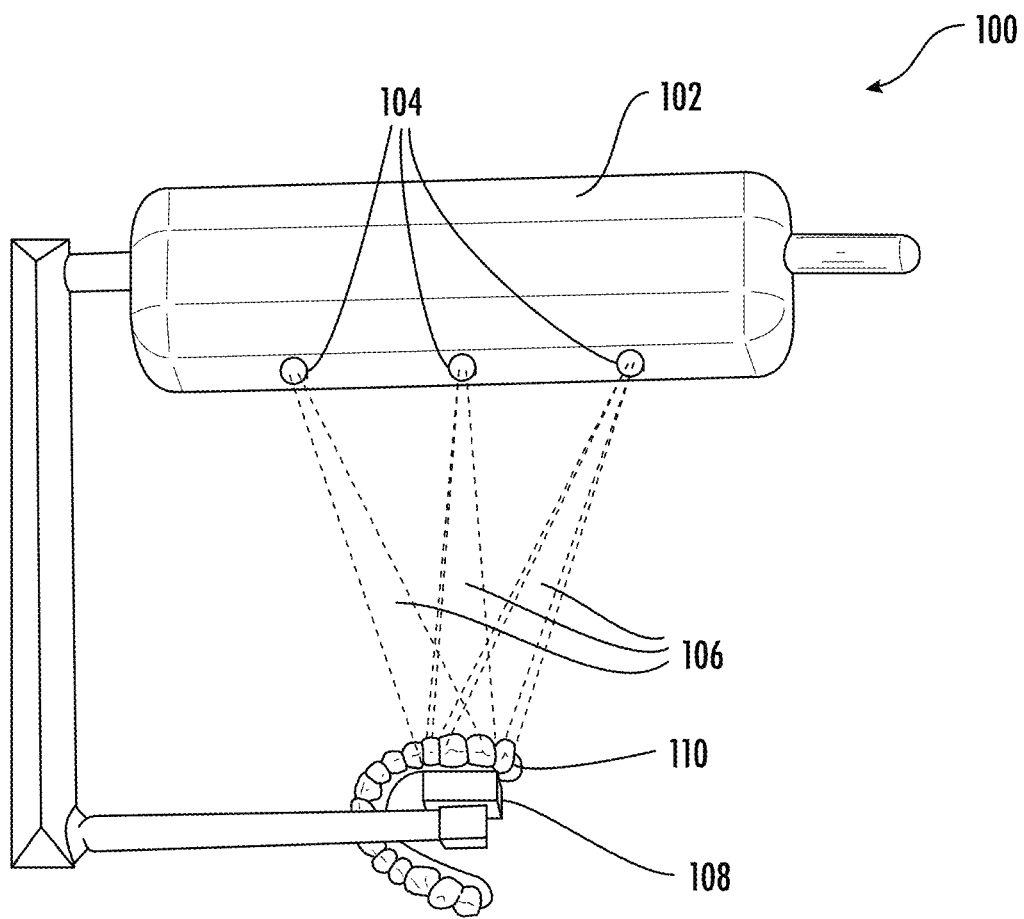
FIG. 1 is a diagram of an intraoral x-ray system that serves as a basis for generating images to be processed by a method and system of some embodiments of the present disclosure.

Intraoral tomosynthesis is an approach to dental imaging capable of capturing some 3D information. During intraoral tomosynthesis, low-dose x-ray projections are collected across a limited angle-span using a pre-determined geometry relative to a digital detector placed inside the mouth. Each projection delivers a fraction of the dose used for a single, standard 2D radiograph. As such, the total dose delivered to the patient during intraoral tomosynthesis is similar to that of standard 2D dental radiography. Although the series of projection views can be obtained by moving a single x-ray source into the necessary locations, perhaps using an optical system to ensure accurate positioning, a multi-source array provides a reliable approach for collecting multiple projection images quickly.

A distributed array of fixed x-ray sources made possible by carbon nanotube-cathode technology has been developed for dental tomosynthesis imaging. Referred to as stationary intraoral tomosynthesis (sIOT), this experimental approach to dental imaging offers a device size, operation, and study time similar to standard 2D dental imaging. This technology was disclosed in the following patents: U.S. Pat. Nos. 9,782,136 and 9,907,520, the disclosures of which are incorporated by reference herein in their entireties. However, regardless of the technique used to acquire the intraoral tomosynthesis scan, computer processing is needed to generate clinically useful images from the information collected at the time of the study. The series of computer algorithms that accomplish each of the necessary processing steps is known as the image processing chain, and the method described hereinbelow is a novel image processing chain that generates multi-view synthetic dental radiographs from intraoral tomosynthesis images.

Multi-view synthetic dental radiographs represent a unique display of the information collected by intraoral tomosynthesis, since this set of computer-generated images recreates what the viewer would see if a series of x-rays were obtained from different viewpoints. In this way, imaging at a dose typical for a single dental radiograph yields multiple computer-generated images that appear to have been taken across a span of angles. There are several advantages to presenting 3D dental x-ray information in this way. First, the synthetic image can be generated from any angle, not just the angles used to acquire the images. Thus, a site-of-concern can be visualized from different perspectives, which can be selected after the scan has been completed. Second, the synthetic images appear similar to standard 2D dental radiographs, and thus, their interpretation does not require additional training or experience. Third, the processing steps used to generate the synthetic images provide an opportunity to remove artifact commonly present in intraoral tomosynthesis images. Finally, analysis of the 3D image space allows for the identification of specific features of interest. These features can then be highlighted in the synthetic images, potentially improving the diagnostic value of the information presented to the reader. As such, the ability to generate multi-view synthetic dental radiographs is anticipated to enhance the clinical utility of intraoral tomosynthesis.

The systems and methods described herein may improve the diagnostic value of dental radiography by providing a novel approach to displaying the information collected by intraoral tomosynthesis, which is a low-dose dental x-ray imaging technique capable of capturing some depth information, using technology that is practical for the dental clinic. More specifically, this disclosure involves a processing method that generates multi-view synthetic dental radiographs. The processes and systems described herein improve the computer related technology of intraoral dental imaging and diagnosis. Since synthetic images are mathematically-generated through computer processing, they can replicate the appearance of an x-ray taken from a range of perspectives, using the information acquired previously at the time of the study. In this way, the intraoral dental imaging technology is improved because when interpreting the images, different viewing perspectives can be selected in order to maximize the display of a specific site-of-concern. In other words, dental lesions and decay that previously could not be seen by traditional dental imaging techniques (without significant x-ray exposure) are more visible using the techniques described herein.

Additionally, the methods and systems disclosed herein improve the computer related technology of dental imaging by helping to minimize the time a dental professional must spend going through multiple 2D images, by emphasizing specific features inside the patient's mouth, and allowing for a faster conclusion by the dental professional. Accomplished by the assistance of software, the systems and methods described herein involve a series of image processing steps, known collectively as the image processing chain. Each step accomplishes a key manipulation of the information in the image, so that when linked together, the result is a clinically-useful set of unique dental images, further improving the computer related technology of intraoral dental imaging.

The image processing chain first constructs a 3D image space from the 2D information available in the set of projection images collected at the time of the study. A forward-projection algorithm then integrates the information in the 3D image stack into a plurality of synthetic dental radiographs that display information from at least two arbitrary viewing angles. In this way, imaging at a dose typical for a single dental radiograph yields multiple computer-generated images that appear to have been taken from different perspectives. Since these perspectives need not be the same as those from which the original x-ray projections were acquired, views can be selected that best display a specific site-of-concern after the study has been completed. This disclosure also includes additional processing steps that may improve the diagnostic value of the final dental images. These additional processing steps can be described generally as filtering, metal-artifact reduction (MAR), and feature of interest enhancement, each customized to dental imaging. Taken in its entirety, this novel method for processing and presenting dental x-ray images has the potential to enhance the clinical utility of intraoral tomosynthesis.

This description should be read in conjunction with the figures, which are designed to illustrate the concepts discussed herein by depicting representative embodiments of the present disclosure. However, since the present disclosure may be embodied in many different forms, the figures should not be construed as limiting the interpretation of the disclosure to a specific embodiment. Similarly, although this written description includes specific terminology for the sake of clarity, this specificity is not intended to limit the interpretation of this disclosure to any particular embodiment.

The subject matter herein discloses a novel method for processing the information acquired by intraoral tomosynthesis, which is a low-dose, limited-angle tomography technique for dental x-ray imaging. This approach to dental imaging allows for the collection of some depth information, using equipment that can be incorporated into a typical dental office. More specifically, the disclosure presented herein is a method that generates a plurality of synthetic dental radiographs, incorporating a unique functionality that allows selection of the viewing perspectives after the scan has been done, regardless of the angle at which the original x-rays were obtained. As such, a viewing angle can be selected that maximizes the display of a site-of-concern, potentially improving the diagnostic value of the dental radiograph.

Assisted by software, the systems and methods of the present disclosure can be applied to any intraoral tomosynthesis system, with intraoral referring to the location of the detector in the mouth, as long as the system includes one or more processors (computers) for implementing the method and a digital monitor to display the final image products. Intraoral tomosynthesis devices work by collecting a series of projection images across a limited angle-span, using a fixed geometry relative to the intraoral detector. The series of projection images can be acquired by a single x-ray source, which is moved into precise locations, perhaps using optical clues for positioning, or by an array of distributed sources. The array of distributed sources can optionally be connected to the detector in some way to lock it into the correct orientation, as depicted in FIG. 1. Regardless of the system used to obtain the tomosynthesis scan, the information available in this set of projection images provides the starting point for the method described herein. This method is a chain of image processing steps, which manipulates the information in the projection images in order to produce a set of synthetic dental radiographs. These descriptions should convey the functionality of the systems and methods presented herein to anyone skilled in the field of dental imaging technology and image processing software.

FIG. 1 is a schematic of an intraoral tomosynthesis device 100. Although FIG. 1 depicts an intraoral tomosynthesis device 100, those having ordinary skill in the art will appreciate that various imaging systems can be used to help perform the processes described herein. Furthermore, although the present disclosure primarily describes the subject matter herein with reference to intraoral tomosynthesis and dental radiographs, those having ordinary skill in the art will appreciate that the systems and methods herein can also be applied to non-dental related imaging. The disclosure herein should not be interpreted as being limited to dental or intraoral related imaging alone. For example and without limitation, the systems and methods described herein can be utilized to perform similar manipulations on tomosynthesis images captured for breast imaging as well as imaging of various other parts of a subject's body. In this depiction, an x-ray source 102 comprising an array of distributed x-ray sources 104 is connected to an intraoral x-ray detector 108, in order to maintain a fixed geometry. In some embodiments, the x-ray source 102 can be disconnected from the intraoral x-ray detector 108. In some embodiments, the intraoral tomosynthesis device 100 is configured to capture x-ray exposures 106 of the subject 110 (i.e., for example and without limitation, a dental patient's teeth or mouth) from multiple angles to provide a set of 2D projection images, which serve as the starting point for the methods and processes described herein.

Figure 2:
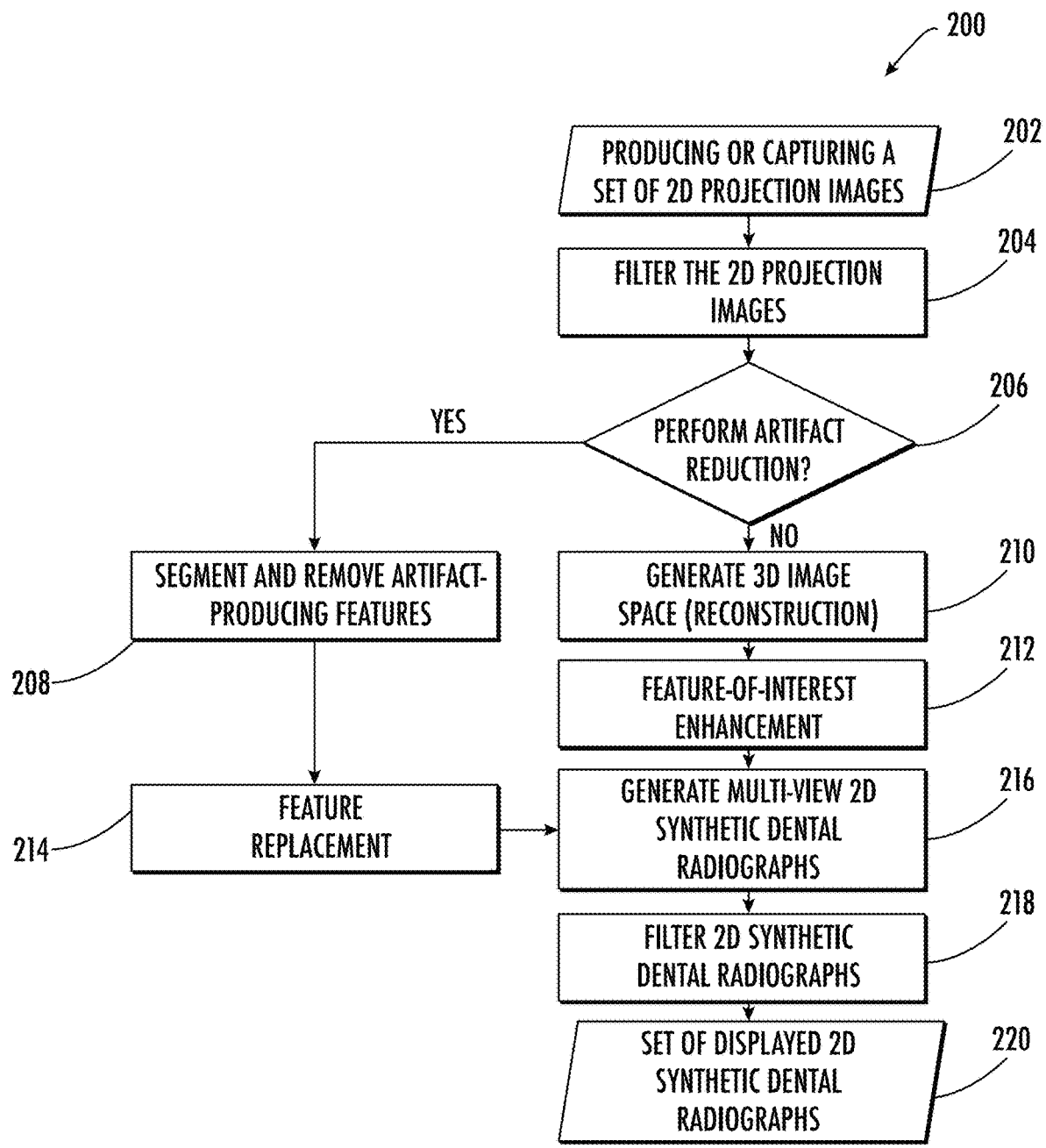
FIG. 2 is a flow chart illustrating an example method of some embodiments of the present disclosure.

Referring to FIG. 2, which illustrates a flow chart depicting steps in a method or an image processing chain 200 that generate multi-view synthetic dental radiographs from the information acquired by an intraoral tomosynthesis scan or other suitable imaging methodology. The purpose of the illustration is to provide a representative embodiment of the image processing chain to demonstrate how each step accomplishes a task upon which the other steps depend. However, since these steps can be connected in different ways and accomplished by various algorithms, FIG. 3 should not be construed so as to limit the interpretation of the disclosure to this specific embodiment. Additionally, those having ordinary skill in the art will appreciate that one, some, or all of the steps in the image processing chain 200 can be performed by one or more processors, including a single central processing unit (CPU) comprising one or more cores. Additionally, each step in the image processing chain 200 can be performed by a separate computer program/subroutine or a single subroutine or computer program function. Moreover, those having ordinary skill in the art will appreciate that steps in the image processing chain 200 can be performed by hardware and/or software, including a centrally positioned processing engine or distributed processing mechanisms. In this way, dedicated processors, hardware, subroutines, application specific integrated circuits (ASICS) or other components can perform some or all of the steps of the image processing chain 200.

In some embodiments, the first step 202 in the image processing chain 200 or method comprises producing or capturing one or more x-ray projections from multiple viewing angles. In some embodiments, the method for capturing the x-ray projections can include using intraoral tomosynthesis. In such an embodiment, the method can further comprise positioning an intraoral x-ray detector in a subject's mouth. Furthermore, the method can comprise determining a position of the intraoral x-ray detector relative to one or more x-ray source. The method can also comprise producing or capturing one or more x-ray projections from multiple viewing angles relative to the intraoral x-ray detector and then transferring the one or more x-ray projection images to one or more processors for processing as discussed further hereinbelow. Although this description explains the subject matter herein with regard to intraoral tomosynthesis, those having ordinary skill in the art will appreciate that other imaging methods may be used as well. In some embodiments, after the x-ray projections are captured or produced, the method comprises generating a plurality of 2D synthetic dental radiographs by manipulating the information contained in the set of x-ray projections acquired at the time of the intraoral tomosynthesis (or other imaging method) scan. This "information" refers to the intensity values measured at each pixel by a digital intraoral x-ray detector, which then transfers the information to computer memory for storage. Once available in the computer, the information can be displayed as a digital image on a monitor, display, or screen, and is also available for manipulation by processing (computer programs or algorithms). The image processing chain 200 described herein works by manipulating these pixel intensity values.

In some embodiments, in the second step 204, the method comprises filtering of the plurality of 2D projection images, customized to the dental image. Such filtering can include, for example, processing to reduce the noise, processing to highlight or segment areas of interest with specific pixel intensities. Filtering can be helpful at this early stage to prepare the pixel intensity values in the projection image for further processing. Additionally, given the significant artifact present around high-contrast features in intraoral tomosynthesis images, these features can be identified and removed, or reduced, from the projection image prior to generating the 3D image space. In some embodiments, in the third step 206, the method of the present disclosure comprises determining whether artifact reduction, for example and without limitation, metal-artifact reduction, is necessary. In some embodiments, the method determines whether artifact reduction is necessary by identifying significant areas of corresponding to presence of high x-ray attenuation materials. If YES, in some embodiments, the image processing chain 200 moves to the fourth step 208. In some embodiments, the processing chain reduces the artifacts by manipulating the pixel values to reduce the impact of the artifacts. One embodiment of this artifact reduction approach is described in detail with the description of FIG. 9.

If artifact reduction is not needed, the image processing chain 200 moves to the fifth step 210 in the process and bypasses the fourth step 208. Additionally, if artifact reduction was necessary, after the reduction has occurred, the image processing chain 200 also moves to the fifth step 210. The information available in the modified (i.e., filtered and/or artifact reduction) projection images can then be used to generate a 3D image space. The processing that generates the 3D image space from the information available in the modified set of 2D projection images is known collectively as "reconstruction." The method presented herein will accept any reconstruction approach, ranging from filtered back projection (FBP) to iterative and/or analytical reconstruction by algebraic or statistical techniques, such as simultaneous iterative reconstruction technique (SIRT), simultaneous algebraic reconstruction technique (SART), or maximum likelihood expectation maximization (MLEM), as long as the processing has been customized to dental imaging, including intraoral tomosynthesis. In some embodiments, the 3D image space is a matrix of voxels or voxel values with calculated intensity values.

Examples of early references for image reconstruction methods include:

FBP: L. A. Feldkamp, L. C. Davis, and J. W. Kress, "Practical cone beam algorithm," J. Opt. Soc. Am. A, vol. 1, pp. 612-9, June 1984.

SIRT: P. Gilbert, "Iterative methods for the reconstruction of three dimensional objects from their projections," J. Theor. Biol., vol. 36, pp. 105-117, 1972.

SART: A. H. Andersen and A. C. Kak, "Simultaneous algebraic reconstruction technique (SART): A superior implementation of the art algorithm," Ultrason. Imaging, vol. 6, pp. 81-94, January 1984.

MLEM: Dempster A, Laird N, and Rubin D, "Maximum likelihood from incomplete data via the EM algorithm, Journal of the Royal Statistical Society, 39, 1-38, 1977.

Once available, the 3D image space provides an opportunity to identify and emphasize features of interest using techniques customized to dental imaging. In some embodiments, the method disclosed herein further comprises a sixth step 212, namely, manipulating the voxel values using various techniques to emphasize the features of interest. Techniques applicable to the method presented herein cover a range of algorithms, such as filters or deep-learning approaches. In general, these algorithms apply a tunable or adjustable weighting function to the 3D image space, in order to identify and/or enhance specific features of interest. For example and without limitation, feature enhancement could include caries enhancement, fracture enhancement, or any other suitable feature enhancement process. As it may occur in different embodiments of this method, the weighting function may sort voxels by intensity and then mathematically emphasize voxels with intensity values typical of the feature of interest, while suppressing voxel values that could obscure the feature of interest, or the weighting function may emphasize different frequency components of the image. As different features, such as caries or fractures, have quite different image properties, the weighting function must have a tunable parameter in order to selectively enhance a specific feature. As an example, if the dentist is concerned about a fracture, weighting to emphasize high-frequency image components may improve the chances of seeing the fracture, which would be detected by its fine edge (a high frequency feature) in the image.

Once the 3D image space is generated, or reconstructed, and feature-of-interest enhancement has occurred, in some embodiments, the method includes an eighth step 216, namely, generating a plurality of multi-view 2D synthetic dental radiographs from the information available in the 3D image space. Additionally, if the image processing chain 200 performed artifact reduction (i.e., went to step four 208), those images go through step seven 214, wherein a feature replacement procedure takes place to enhance the areas around where the artifact reduction took place. Additionally, in some embodiments, the method includes a ninth step 218, namely, filtering the 2D synthetic dental radiographs to improve the display of one or more features of interest. Such filtering steps may include, but are not limited to, smoothing by noise reduction, sharpening by edge enhancement, and histogram rebalancing for feature of interest enhancement. Finally, in the tenth step 220, once the plurality of 2D synthetic dental radiographs have been processed, all or a subset of them can be displayed on a display for a dental professional or other person to view.

Figure 3:
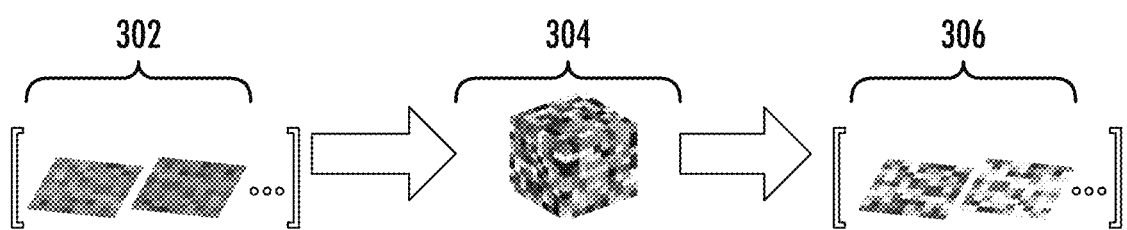
FIG. 3 illustrates a visual depiction of some steps in the process of some embodiments of the present disclosure.

Referring to FIG. 3, which depicts a logical diagram of a subset 300 of the steps taken in the image processing chain. In some embodiments, as described herein, the image processing chain uses the 2D information 302 available in the set of projection images acquired at the time the dental images are captured to mathematically generate a 3D image space 304. The 3D image space 304, described in more detail hereinbelow, is a mathematical construct that contains the information needed to create the synthetic dental radiographs. Additional algorithms, such as filtering, artifact reduction, and feature enhancement can be incorporated to improve the display of one or more features of interest, as described below. Once the 3D image space 304 is generated, a set of multi-view dental radiographs 306 can be synthetically generated (i.e., by one or more processors) from the 3D image space 304.

Referring to FIG. 4A and FIG. 4B, which illustrate flow charts depicting small differences between generating various feature enhanced images, including carries-enhanced synthetic radiographs 400A and fracture-enhanced synthetic radiographs 400B. In the carries-enhanced synthetic radiographs flow chart 400A, as described above, the first step in the process 402A is capturing or generating intraoral projection images. Once the images have been captured, they are reconstructed 404A, as described herein, into a 3D image space or 3D image stack 406A. From there, in some embodiments, the 3D image stack 406A is processed and filtered 408A, as described herein, to enhance features that detail caries in the teeth. In some embodiments, in order to better emphasize and enhance any caries in the subject, the process can comprise selectively emphasizing lower-frequency components, which can improve the visibility of caries. The caries-enhanced image stack 410A can then be forward projected 412A, for example and without limitation, onto a monitor, display, or screen for a dentist, dental hygienist, doctor, or other viewer to view one or 2D caries-enhanced synthetic radiographs 414A, where, each of the radiographs are synthesized by one or more processors from the caries-enhanced 3D image stack 410A.

The method for generating fracture-enhanced synthetic radiographs 400B is almost identical to the method for generating caries-enhanced synthetic radiographs 400A. However, in some embodiments, in the method for generating fracture-enhanced synthetic radiographs 400B, instead of filtering to enhance caries 408A, the method for generating fracture-enhanced synthetic radiographs 400B includes filtering to isolate the background of the images 408B, such as selecting low frequency components and or thresholding pixel values. Additionally, the image can be filtered, for example, by selectively emphasizing the higher-frequency components of the image, which can improve the visibility of small fractures. Once filtered, the background-isolated 3D image stack 410B can be selected to enhance some features such as fractures. The feature enhanced 3D images stack together with background overlap tissue images 414B then can be forward projected to generate 2D fracture-enhanced synthetic radiographs 416B.

Figure 5:
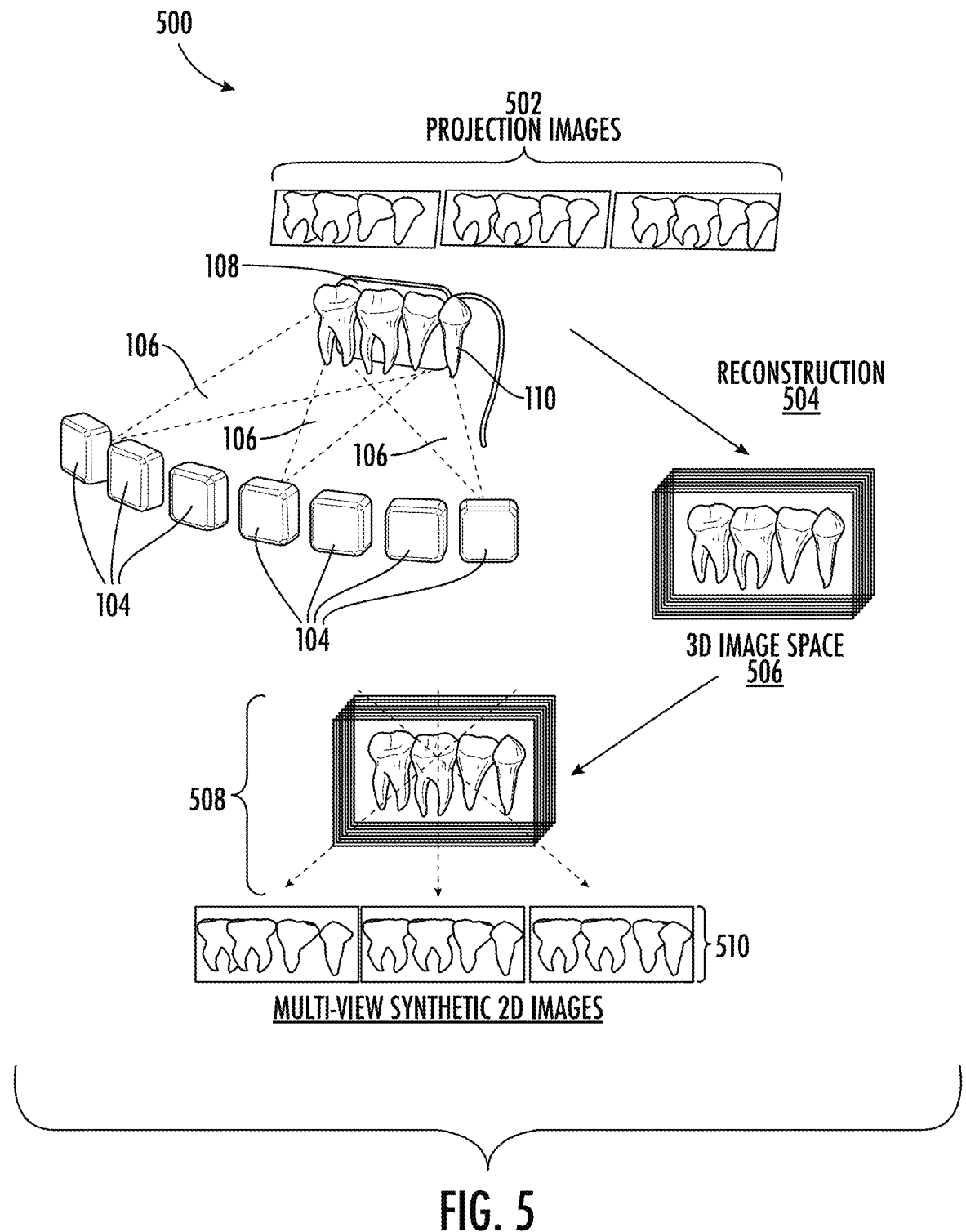
FIG. 5 illustrates visual representations of several steps in the process of some embodiments of the present disclosure.

Referring to FIG. 5, which illustrates another depiction of some steps in the image processing chain of the present disclosure as well as how they interact with physical structures of an x-ray imaging system. The system illustration 500 depicts both physical structures and virtual processes that make up parts of the methods and systems of the present disclosure. For example and without limitation, the array of spatially distributed x-ray sources 104 can be configured to expose the subject 110 to x-ray radiation 106 at different angles, generating one or more intraoral tomosynthesis projection images 502. The projection images 502 are captured by the detector 108 (not visible in this view, but positioned behind the subject 110) and transmitted to one or more processors (not shown in this view) for processing.

In some embodiments, the one or more processors are configured for reconstructing the one or more intraoral tomosynthesis 2D projection images into a 3D image space 506. Once the 3D image space 506 is created and the various filtering and manipulations of the data in the 3D image space 506 described herein are complete, the one or more processors is configured to digitally generate one or more multi-view synthetic 2D images 510 from various angles of the manipulated 3D image space 508.

FIG. 5 further illustrates an example of the step in the image processing chain that generates the multi-view synthetic dental radiographs from the enhanced information now present in the 3D image space. Since the information present in the 3D image space can be projected into a synthetic dental radiograph from any arbitrary angle, this method provides a unique approach to displaying dental images by replicating how a standard 2D radiograph would appear if it had been obtained from the selected viewing angle. By providing a range of perspectives, a set of synthetic images can best display a specific site-of-concern.

Again, as described above, the disclosure herein should not be interpreted as being limited to dental or intraoral related imaging alone. For example and without limitation, the systems and methods described herein can be utilized to perform similar manipulations on tomosynthesis images captured for breast imaging as well as imaging of various other parts of a subject's body.

Figure 6:
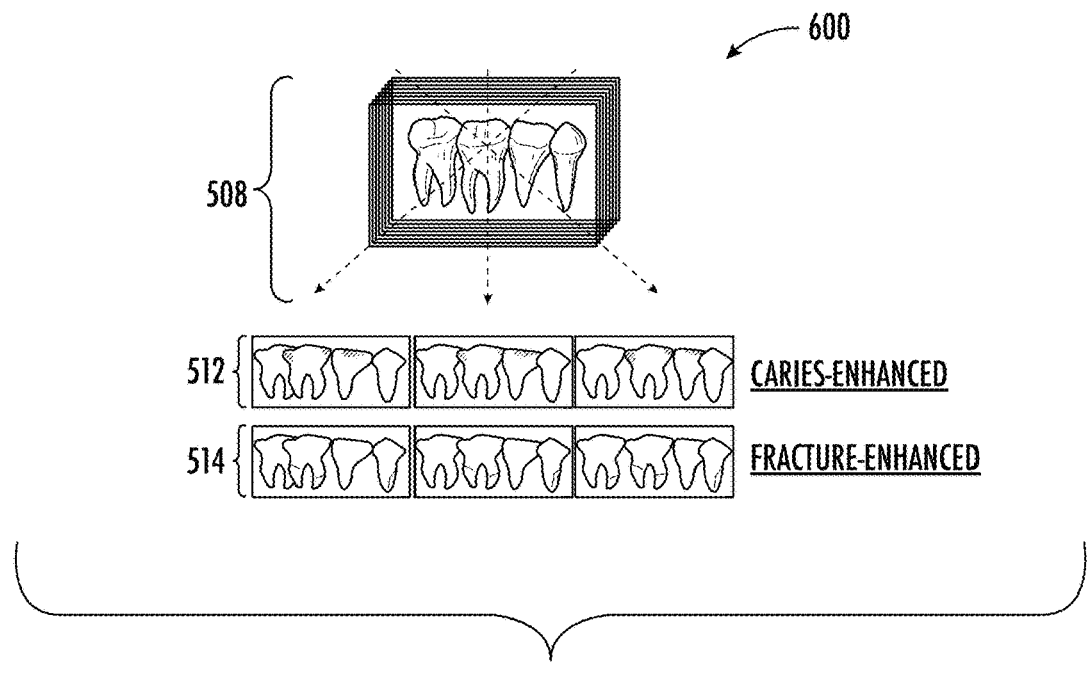
FIG. 6 illustrates how viewing a 3-dimensional (3D) image space, developed by steps in the process of the present disclosure, from different angles can result in various details of the images becoming more clear.

Referring to FIG. 6, which illustrates the effects of applying a tunable weighting function to the 3D image space in order to enhance specific features of interest. FIG. 6 is a partial system illustration 600 of the system and methods of the present disclosure. As depicted in FIG. 6, multi-view synthetic 2D dental radiographs can be generated from the manipulated 3D image space 508 from multiple angles to provide additional feature enhancements compared to that in FIG. 5. For example, selectively emphasizing the higher-frequency components of the image may improve the visibility of small fractures, whereas emphasizing lower-frequency components may improve the visibility of caries. The application of each weighting function produces a unique set of multi-view synthetic dental radiographs. In other words, based on the manipulation of the data in the 3D image space, caries enhanced images 512 and/or fracture-enhanced images 514 can be generated.

Figure 7:
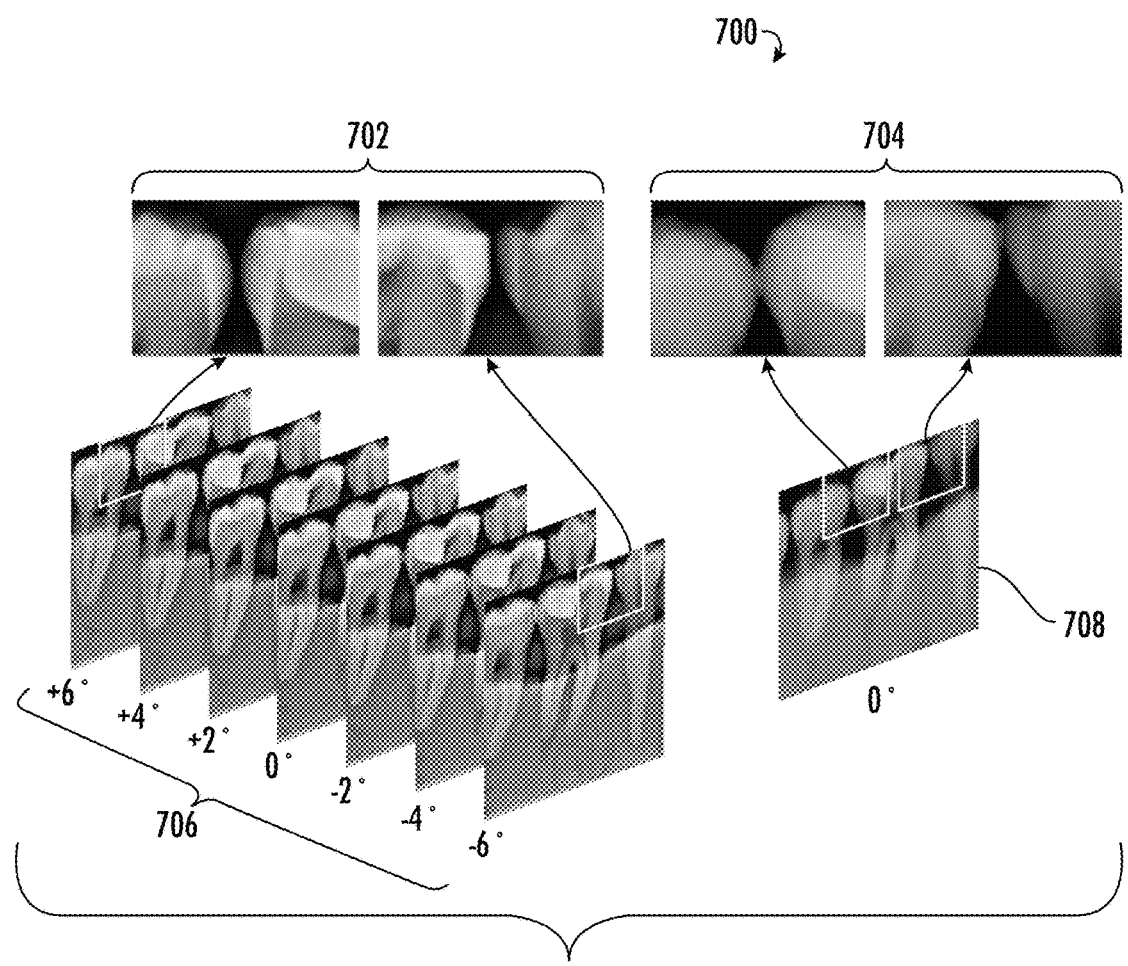
FIG. 7 illustrates how synthetic radiographs, generated by various embodiments of the present disclosure, give more details about the imaged subject as compared to standard radiographs.

Referring to FIG. 7, which depicts comparisons 700 between synthetic radiographs 702, generated using systems and methods according to some of the embodiments of the present disclosure, and standard radiographs 704, generated according to previously available techniques. As depicted in the comparison pictures, the synthetic radiographs 702 show more detail such that additional caries and dental disease/lesions can be found and distinguished from healthy tissue. As depicted in FIG. 7, the synthetic radiographs 702 can be generated from multiple angles 706 with respect to a particular region or perspective. The standard radiograph 704 on the other hand cannot be generated from multiple angles, it is generated from a single angle 708. As can be seen in from the multiple angles 706, the tooth surfaces in the region where two teeth come into contact can be separated only in certain view angles of the synthetic radiographs 702, which are available only in synthetic radiograph images. Whereas, in standard radiographs 704, the overlap surfaces blur the teeth boundary thus inhibiting the proper diagnosis of potential carries in the region.

Figure 8A:
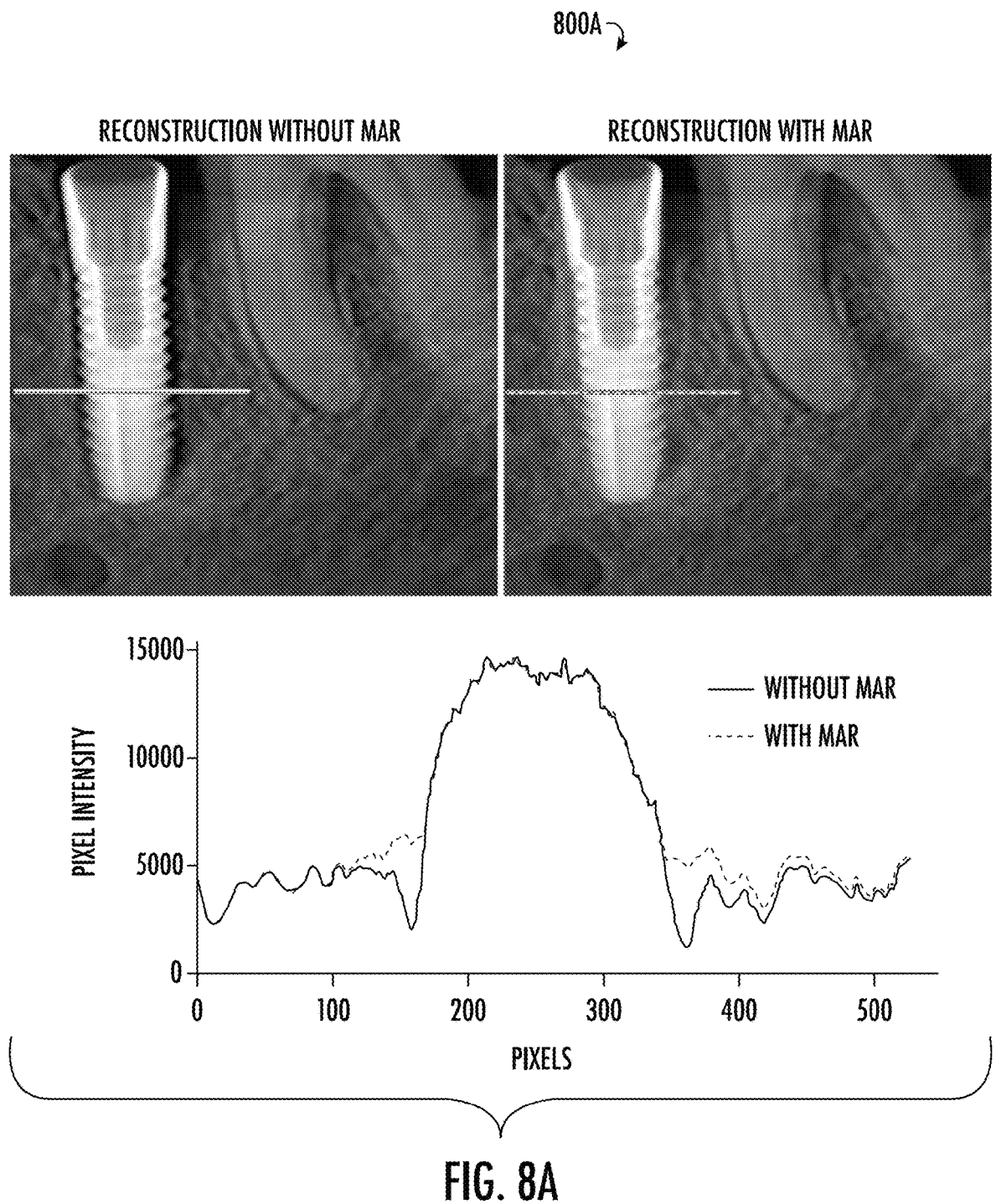
FIG. 8A and FIG. 8B illustrate how processing x-ray images using metal artifact reduction (MAR) can better reveal dental pathology surrounding and/or near metals in the x-ray image.
Figure 8B:
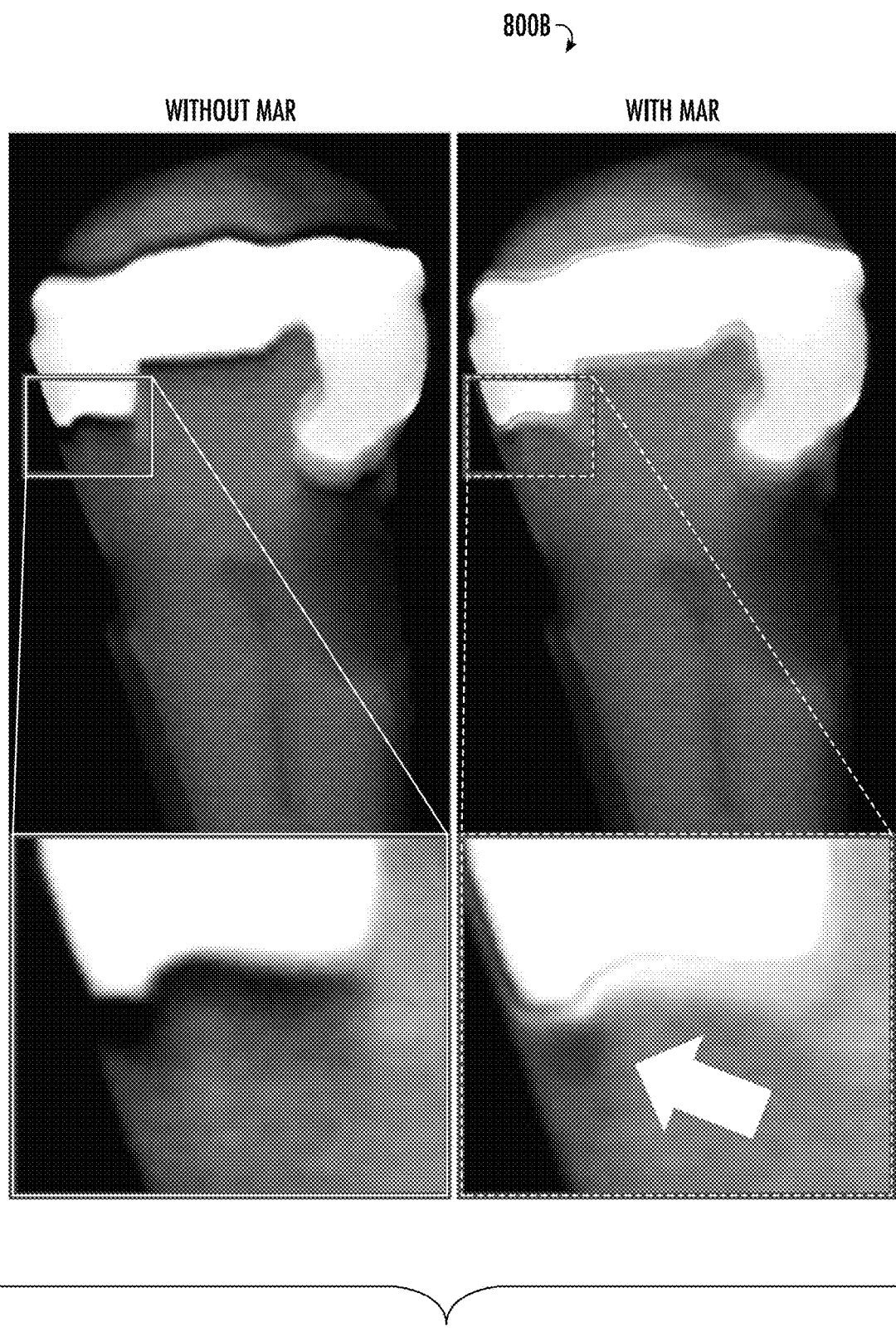

Referring to FIG. 8A and FIG. 8B, further comparisons 800A and 800B between images that are reconstructed with metal-artifact reduction (MAR) and without MAR are provided. As shown in comparison 800A when the image is reconstructed using MAR, the tissue around the implant screw is much more visible and pathology is much more visible as compared to the image not reconstructed using MAR. The graph below the comparison images 800A indicate the difference in pixel intensity between the image with and without MAR. As shown, the pixel intensity without MAR is much lower around the edges of the screw than the pixel intensity with MAR. Comparison 800B illustrates a zoomed-in radiograph where the image with MAR clearly identifies tooth decay underneath the metal filling (bright white amorphous shape) whereas the image without MAR is unclear as to whether decay is present. At a minimum, the image without MAR indicates a significant amount of false positives that would likely lead a professional to ignore the area because of the likelihood of metal-artifact skewing the image.

Figure 8C:
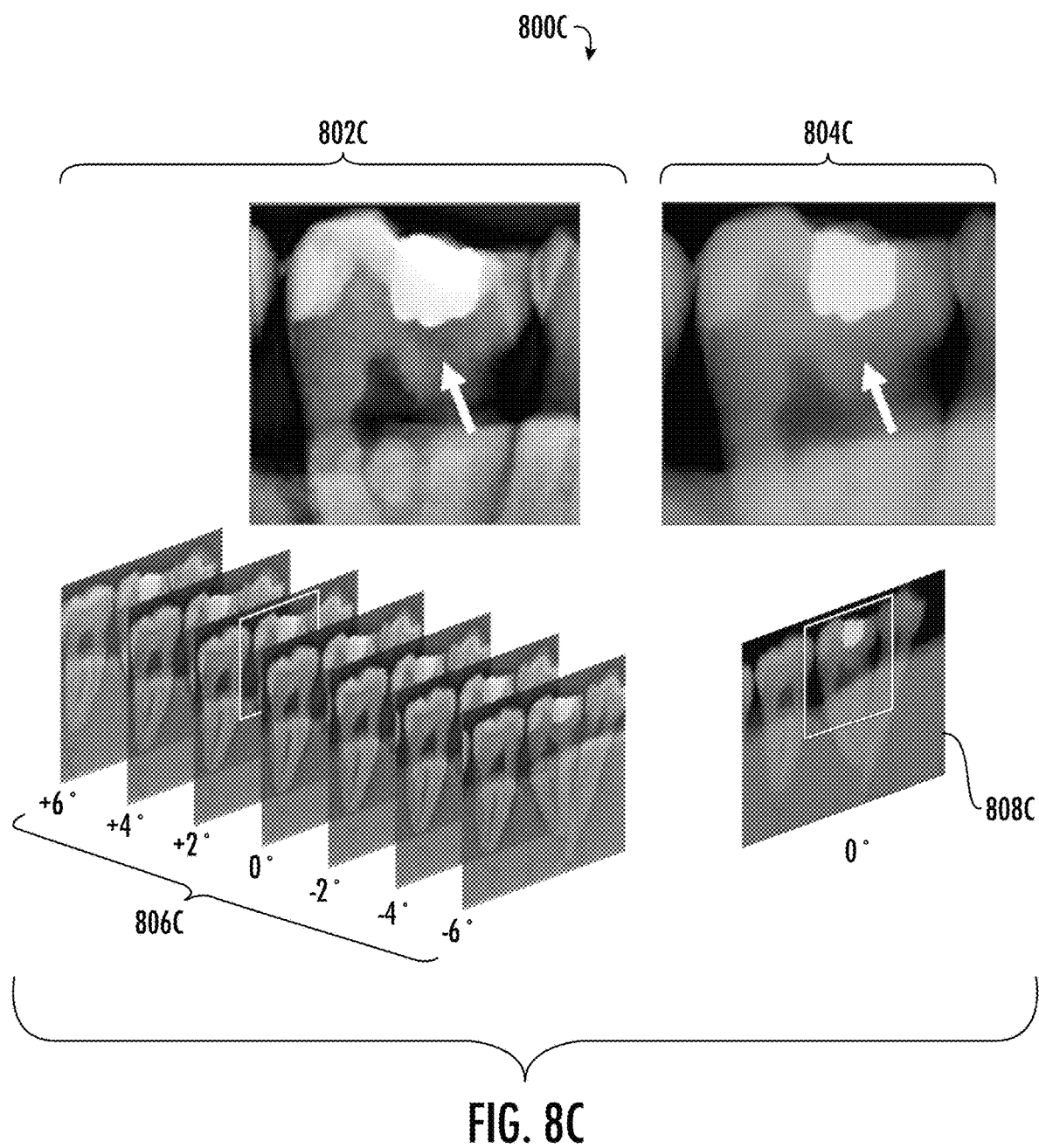
FIG. 8C and FIG. 8D illustrate how synthetic radiographs, generated by various embodiments of the present disclosure, can emphasize more details about the imaged subject as compared to standard radiographs.
Figure 8D:
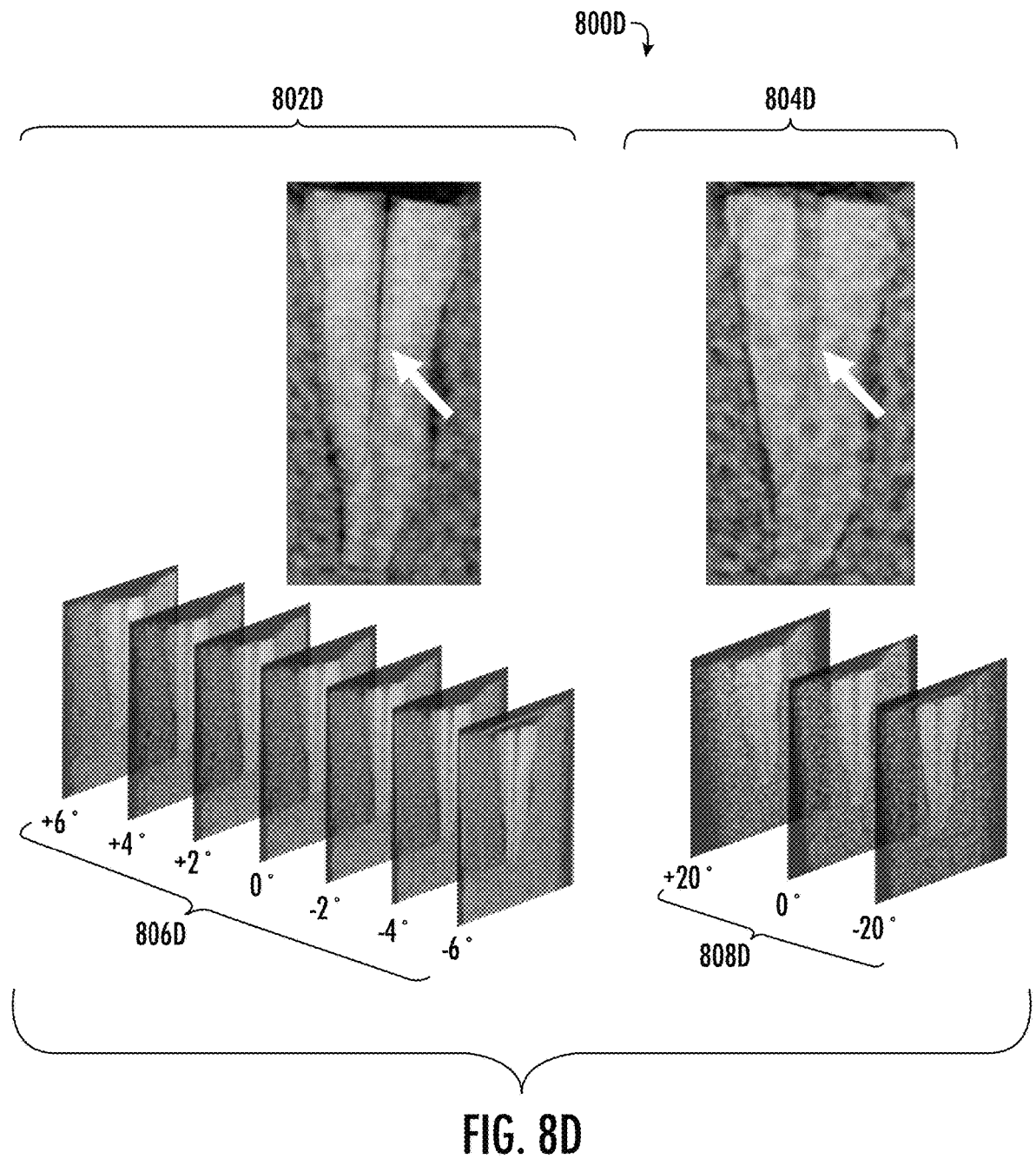

Referring to FIG. 8C and FIG. 8D, more comparisons 800C and 800D between synthetic radiographs 802C and 802D and standard radiographs 804C and 804D are depicted. In FIG. 8A, the comparison 800C is made to illustrate how metal-artifact reduction, part of the filtering processes of the image processing chain of the present subject matter, can be used to better reduce metal artifacts around metal objects in the mouth (e.g., screws, fillings, surgical implants, etc.) and give the professional viewing the synthetic radiographs 802C a better visualization of the subject being imaged. Those having ordinary skill in the art can readily appreciate that the areas around the filling in the synthetic radiograph 802C is much more clearly defined and is comparable to the standard radiograph 804C taken of the same tooth.

As depicted in FIG. 8D, the comparison 800D here shows how fracture enhancement filtering can give more detail on a fracture in the imaged subject. As depicted in the synthetic radiograph 802D, there is a clearly defined and distinct line or crack running down the tissue. The crack or line is not so clearly visible in the standard radiograph 804D.

Figure 9:
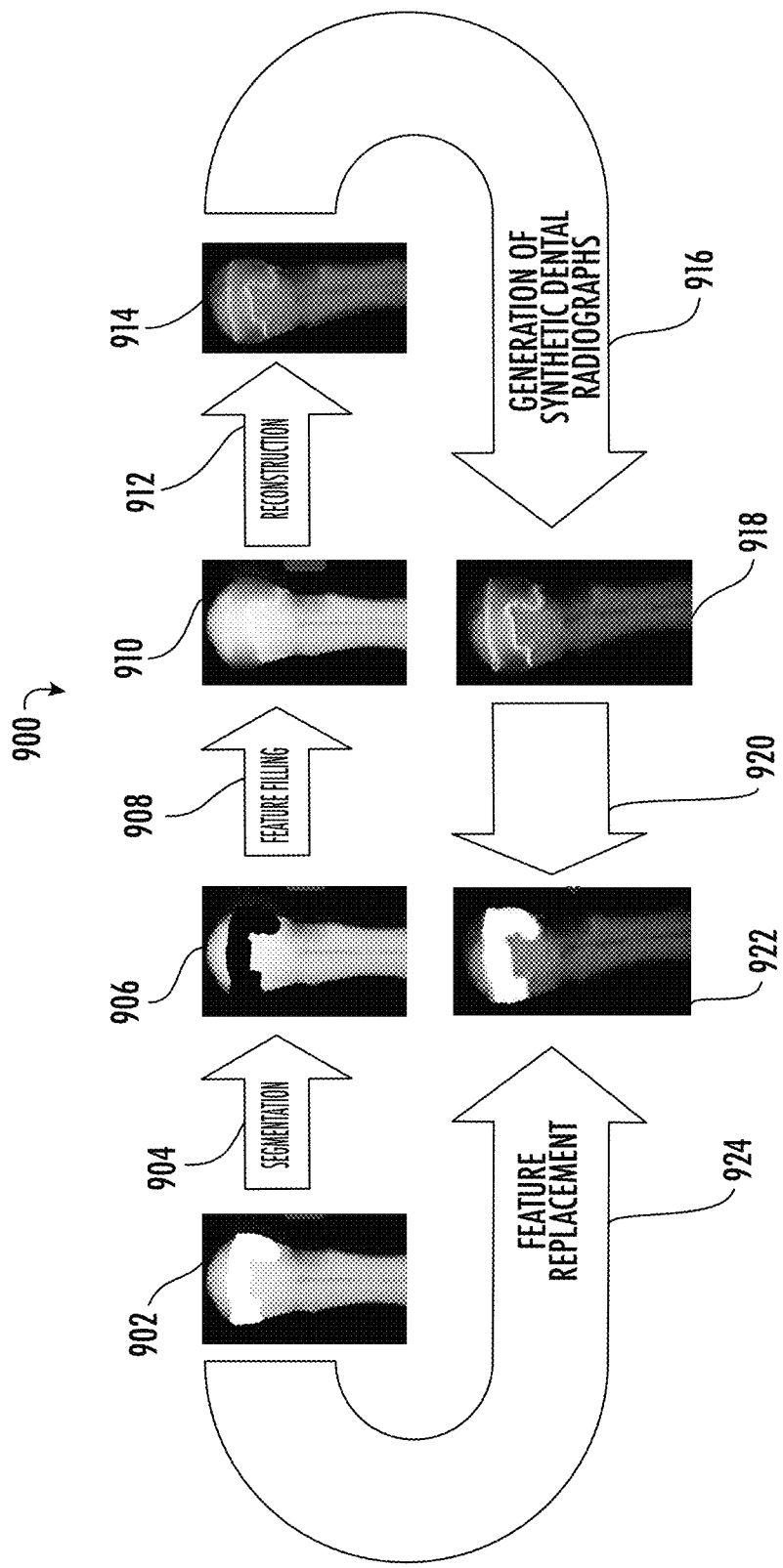
FIG. 9 illustrates how various steps in the process of some embodiments of the present disclosure affect a projection image of a tooth.

FIG. 9 is a flow chart 900 depicting changes in the image information as images are manipulated by some of the processing steps of an artifact reduction approach, as these changes would appear to a viewer during an embodiment of the present disclosure. However, since there are potentially many approaches to accomplishing artifact reduction, including different techniques to complete each of the key steps, as well as different locations within the overall image processing chain where these steps can be applied, the figure should not be construed as limiting the interpretation of the present disclosure to this specific embodiment. Artifact reduction is important when developing an image processing chain for intraoral tomosynthesis, given the frequent presence of artifact-producing objects in the mouth, including metal such as amalgam and implant posts. These artifacts, which can hide pathology, are the result of the processing required to generate the 3D image space and can be amplified by the algorithms which generate the final synthetic images. As such, artifact reduction techniques are needed in some embodiments to minimize these artifacts in order to maximize the clinical value of the displayed images. As shown in the representative approach in FIG. 9, artifact reduction begins at the level of the projection images. The first image 902, represents such an example 2D projection image captured by means of, for example and without limitation, intraoral tomosynthesis.

Once the first image 902 is captured, the process continues with the segmentation 904 and then removal of the pixel values corresponding to an artifact-producing feature. "Segmentation" refers to identifying the pixels which make up a particular feature such as an artifact-producing feature. A host of segmenting approaches customized for the dental image can be envisioned, all of which would be applicable with the method presented herein. For example, as many features in dental images have a high contrast relative to their background and contain sharp edges, one embodiment of this method may include edge-detecting segmentation approaches involving thresholding and/or thresholding the gradient magnitude of the image to identify the pixels that define a feature and/or its boundary, respectively, with "thresholding" referring to the identification of pixels that have an intensity value above a defined level, and the "gradient magnitude" representing the relative change between pixel values in the image. The second image 906 in the flow chart 900 illustrates a segmented 2D projection image, segmented according to some embodiments of the present disclosure.

Following segmentation, the artifact-producing feature's pixel values must be replaced in order to proceed through the image processing chain. Therefore, the features must be filled in during a feature filling step 908. Methods such as interpolation-based in-painting can be used to estimate appropriate pixel values for the feature filling step 908. For example, and without limitation, pixel values can be assigned to segmented regions by inward interpolation from surrounding pixel values for each of the 2D projection images (i.e., the images before they are reconstructed into the 3D image space). However, the features removed from the projection images can have diagnostic value, and as such, in some embodiments, they must be returned to the final synthetic images prior to their display. Once the features are filled in, the image will look similar to the third image 910. This represents one of the 2D projection images that will be reconstructed 912 into the 3D image space. The fourth image 914 depicts an example slice from the 3D image space after the reconstruction 912 stage. Once the 3D image space is created, the synthetic dental radiographs are generated 916. In this representation, the synthetic dental radiographs include features that are filled in. Using the locations of the segmented pixels in the original projection images, the features can be replaced in the synthetic dental radiographs, with an orientation and appearance appropriate to the selected viewing angle used to generate the synthetic images. The fifth image 918 illustrates a synthetic dental radiograph with filled-in features.

The synthetic dental radiographs can be optimized by applying additional filtering to improve the quality of the final images. As may be seen in some embodiments of this method, the filtering will involve a string of customized and complementary filters, which the reader can select for a specific dental imaging task. As an example, in order to maximize the display of a tooth fracture, edge-preserving low pass filtering to reduce noise may need to be combined with high-pass filtering to emphasize the fracture edge. Before the final synthetic dental radiographs are ready for display, some of the features, such as, for example and without limitation, fillings or implants, are replaced 920 and 924. This step includes inspecting the original projection image (i.e. the first image 902) to determine the details of the feature to be replaced. Finally, the sixth image 922 illustrates what the final synthetic dental radiograph would look like after all filtering and manipulation is complete. The set of final synthetic images are then displayed to a viewer, such as for example and without limitation, a dental professional, for them to view.

Figure 10:
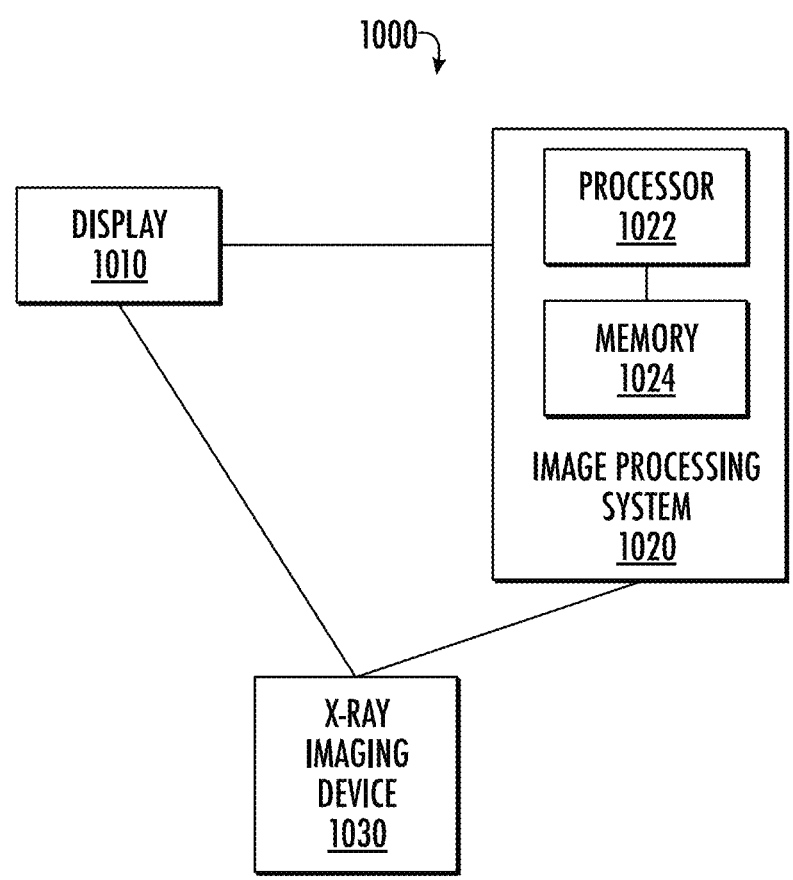
FIG. 10 illustrates a block diagram of various components of an x-ray imaging and processing system according to some embodiments of the present disclosure.

Referring to FIG. 10, which illustrates a topology diagram of a system 1000 of the present disclosure. For example and without limitation, the system 1000 can comprise an x-ray imaging device 1030 configured to capture one or more x-ray images of a subject, as described with respect to FIG. 1. In some embodiments, the x-ray imaging device 1030 is in communication with a display 1010 and/or an image processing system 1020. In some embodiments, the image processing system 1020 is configured to receive, via wireless or wired connection, one or more 2D projection images from the x-ray imaging device 1030. As described above, the 2D projection images can be taken from different angles with respect to the subject and transmitted to the image processing system 1020 from the x-ray imaging device 1030.

In some embodiments, the image processing system 1020 comprises one or more processors 1022 and non-transitory, computer-readable memory 1024. In some embodiments, the one or more processors can be configured to manipulate the 2D projection images according to the various processes described hereinabove. Those having ordinary skill in the art will appreciate that the memory 1024 can be used to store image data, executable instructions for performing the various processes described above, or any other suitable data. In some embodiments, the one or more processors 1022 can comprise a single processor with multiple cores, or multiple distinct processors. Once the processor 1022 has completed manipulating the images, as described above, the image processing system 1020 is configured to transmit the images to the display 1010. In some embodiments, those having ordinary skill in the art will appreciate that the image processing system 1020 can be configured to transmit the manipulated images to the display 1010 when a viewer requests the images via buttons or some other tool on the display 1010. In some other embodiments, the image processing system 1020 can be configured to automatically transmit the manipulated images to the display 1010 after the image manipulation processes are complete.

Additionally, the display 1010 is configured to receive x-ray images from either the x-ray imaging device 1030 (i.e., non-manipulated images) or one or more synthetic dental radiographs from the image processing system 1020 (i.e., x-ray images manipulated according to the processes described herein). Once received, the display 1010 can be configured to display one or more of the received images based on automatic or manual request from the viewer.

The present description also discloses a system for generating or producing one or more multi-view synthetic dental radiographs. In some embodiments, such a system can comprise a display in communication with an image processing system comprising one or more processors and a computer readable medium such as memory or random-access memory (RAM). In some embodiments, the imaging processing system can be configured to implement the method described herein above. In some embodiments, the image processing system can be combined with an intraoral tomosynthesis device or other x-ray machine to create a whole system that not only captures the x-rays but also processes the images according to the steps discussed hereinabove. In some embodiments, the system for generating one or more multi-view synthetic dental radiographs can be separate and apart from an intraoral tomosynthesis machine or other x-ray machine.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A method for generating one or more multi-view synthetic dental radiographs using a chain of interdependent image processing steps, the method comprising:
   generating or receiving a plurality of two-dimensional (2D) projection images;
   manipulating pixel values contained in each of the plurality of 2D projection images by:
      segmenting artifact-producing features in each of the plurality of 2D projection images; and
      assigning pixel values to segmented regions by inward interpolation from surrounding pixel values for each of the plurality of 2D projections, thereby reducing imaging artifacts caused by the artifact-producing features;
   reconstructing a three-dimensional (3D) image space from information available in the plurality of 2D projection images, the 3D image space comprising voxel values;
   manipulating the voxel values in the 3D image space using one or more tunable weighting algorithms that can be adjusted to emphasize one or more features of interest of each image in the 3D image space;
   generating a plurality of synthetic dental radiographs from multiple views using information available in the 3D image space;
   fusing the artifact-producing features segmented from the plurality of 2D projection images into the plurality of synthetic dental radiographs to produce a set of final synthetic dental radiographs that comprise the artifact-producing features; and
   displaying one or more synthetic dental radiographs of the set of final synthetic dental radiographs that comprise the artifact-producing features;
   wherein the artifact-producing features are segmented in each of the plurality of 2D projection images prior to reconstructing the 3D image space.

2. The method of claim 1, further comprising manipulating pixel values in the plurality of synthetic dental radiographs.

3. The method of claim 1, wherein the artifact-producing features are formed by metal objects in a subject's teeth.

4. The method of claim 3, wherein the metal objects comprise screws, fillings, surgical implants, and/or amalgam.

5. The method of claim 1, wherein the 3D image space is generated using analytical or iterative reconstruction algorithms customized to intraoral tomosynthesis.

6. The method of claim 1, further comprising identifying and/or enhancing features of interest, using filters and/or deep-learning techniques, features of interest including dental caries or dental fractures in the 3D image space.

7. The method of claim 1, wherein the plurality of synthetic dental radiographs represent a range of viewing perspectives that may or may not depict a same angle from which the original x-ray projections were acquired.

8. The method of claim 1, wherein different weighting algorithms are applied to the 3D image space to enhance features of interest, such as caries or fractures, with each weighting algorithm producing a unique set of multi view synthetic dental radiographs.

9. The method of claim 8, wherein enhancing fractures comprises emphasizing higher-frequency components of an image and enhancing caries comprising emphasizing lower-frequency components of the image.

10. The method of claim 1, further comprising optimizing the plurality of synthetic dental radiographs using filters customized to dental imaging.

11. The method of claim 1, wherein reconstructing the 3D image space comprises using one or more of the following reconstruction techniques: filtered back projection (FBP), simultaneous iterative reconstruction technique (SIRT), simultaneous algebraic reconstruction technique (SART), or maximum likelihood expectation maximization (MLEM).

12. A method for generating one or more multi-view synthetic dental radiographs, the method comprising:
   positioning an intraoral x-ray detector in a subject's mouth;
   determining a position of the intraoral x-ray detector relative to one or more x-ray source;
   capturing one or more x-ray projections from multiple viewing angles relative to the intraoral x-ray detector;
   transferring the one or more x-ray projection images to one or more processors;
   manipulating, by the one or more processors, pixel values contained in the one or more x-ray projection images by:
      segmenting artifact-producing features in each of the plurality of 2D projection images; and
      assigning pixel values to segmented regions by inward interpolation from surrounding pixel values for each of the plurality of 2D projections, thereby reducing imaging artifacts caused by the artifact-producing features;
   reconstructing a 3D image space from information available in the one or more x-ray projection images, the 3D image space comprising voxel values;
   manipulating the voxel values in the 3D image space using one or more tunable weighting algorithms that can be adjusted to highlight specific image features in each image in the 3D image space;
   generating a plurality of synthetic dental radiographs from multiple views using information available in the 3D image space;
   fusing the artifact-producing features segmented from the plurality of 2D projection images into the plurality of synthetic dental radiographs to produce a set of final synthetic dental radiographs that comprise the artifact-producing features; and
   displaying one or more synthetic dental radiographs of the set of final synthetic dental radiographs that comprise the artifact-producing features;
   wherein the artifact-producing features are segmented in each of the plurality of 2D projection images prior to reconstructing the 3D image space.

13. A system for generating one or more multi-view synthetic dental radiographs comprising:
   an image processing system comprising one or more processors; and
   a display in communication with the image processing system;
   wherein the image processing system is configured to:
      receive a plurality of two-dimensional (2D) projection images;
      manipulate pixel values contained in each of the plurality of 2D projection images by:
         segmenting artifact-producing features in each of the plurality of 2D projection images; and
         assigning pixel values to segmented regions by inward interpolation from surrounding pixel values for each of the plurality of 2D projections, thereby reducing imaging artifacts caused by the artifact-producing features;
      reconstruct a three-dimensional (3D) image space from information available in the plurality of 2D projection images, the 3D image space comprising voxel values;
      manipulate the voxel values in the 3D image space using one or more tunable weighting algorithms that can be adjusted to emphasize features of interest of each image in the 3D image space;
      generate a plurality of synthetic dental radiographs from multiple views using information available in the 3D image space;
      fuse the artifact-producing features segmented from the plurality of 2D projection images into the plurality of synthetic dental radiographs to produce a set of final synthetic dental radiographs that comprise the artifact-producing features; and
      display one or more synthetic dental radiographs of the set of final synthetic dental radiographs, which comprise the artifact-producing features, on the display;
      wherein the artifact-producing features are segmented in each of the plurality of 2D projection images prior to reconstructing the 3D image space.

14. The system of claim 13, wherein the artifact-producing features are formed by metal objects in a subject's teeth.

15. The system of claim 14, wherein the metal objects comprise screws, fillings, surgical implants, and/or amalgam.

16. The system of claim 13, wherein the 3D image space is generated using analytical or iterative reconstruction algorithms customized to intraoral tomosynthesis.

17. The system of claim 13, wherein the image processing system is further configured to identify and/or enhance features of interest, using filters and/or deep-learning techniques, including dental caries or dental fractures in the 3D image space.

18. The system of claim 13, wherein the plurality of synthetic dental radiographs represent a range of viewing perspectives that may or may not depict a same angle from which the original x-ray projections were acquired.

19. The system of claim 13, wherein the image processing system is further configured to apply different weighting algorithms to the 3D image space to enhance features of interest, such as caries or fractures, with each weighting algorithm producing a unique set of multi-view synthetic dental radiographs.

20. The system of claim 19, wherein the image processing system is configured to:
   enhance fractures by emphasizing higher-frequency components of an image; and
   enhance caries by emphasizing lower-frequency components of an image.

21. The system of claim 13, wherein the image processing system is further configured to optimize the plurality of synthetic dental radiographs using filters customized to dental imaging.

22. The system of claim 13, wherein the image processing system is configured to reconstruct the 3D image space using one or more of the following filter techniques: filtered back projection (FBP), simultaneous iterative reconstruction technique (SIRT), simultaneous algebraic reconstruction technique (SART), or maximum likelihood expectation maximization (MLEM).

* * * * *